United States Patent [19]

Morris et al.

[11] 4,225,726
[45] Sep. 30, 1980

[54] CATALYTIC CONDENSATION OF ALDEHYDES TO 1,3-GLYCOL MONOESTERS

[75] Inventors: Don L. Morris; Anthony W. McCollum, both of Longview, Tex.

[73] Assignee: Eastman Kodak Company, Rochester, N.Y.

[21] Appl. No.: 41,833

[22] Filed: May 23, 1979

[51] Int. Cl.$^2$ .............................................. C07C 67/44
[52] U.S. Cl. .............................. 560/238; 260/340.7; 260/410; 260/410.5; 260/410.6; 560/1; 560/100; 560/101; 560/105; 560/106; 560/107; 560/112; 560/118; 560/122; 568/461; 568/496
[58] Field of Search ............... 560/238, 105, 106, 107, 560/112, 100, 101, 118, 122, 1; 260/410.6, 410.5, 410

[56] References Cited

U.S. PATENT DOCUMENTS

| | | | |
|---|---|---|---|
| 2,403,876 | 7/1946 | Nord | 560/238 |
| 3,291,821 | 12/1966 | Perry et al. | 560/238 |

Primary Examiner—Vivian Garner
Attorney, Agent, or Firm—Edward R. Weber; Daniel B. Reece, III

[57] ABSTRACT

This invention relates to an improved method for the catalyzed condensation of aldehydes in the liquid phase to form 1,3-glycol monoesters utilizing tin metal or a tin oxide catalyst. Condensation can be visualized as an aldol condensation followed by a Tischenko reaction between the aldol and a third molecule of aldehyde. In its simplest form the condensation can be illustrated by the following general formula

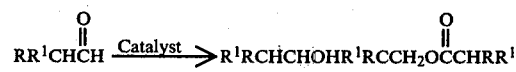

R or R$^1$=Hydrogen or alkyl group of 1 to 20 carbon atoms or aromatic groups. R and R$^1$ can also be part of a cyclic system.

7 Claims, No Drawings

CATALYTIC CONDENSATION OF ALDEHYDES TO 1,3-GLYCOL MONOESTERS

This invention describes an improved process for the condensation of aldehydes in the liquid phase to form 1,3-glycol monoesters utilizing a tin metal or a tin oxide catalyst. Condensation can be visualized as an aldol condensation followed by a Tischenko reaction between the aldol and a third molecule of aldehyde. In its simplest form the condensation can be illustrated by the following general formula

R and $R^1$ are Hydrogen or alkyl group of 1 to 20 carbon atoms or aromatic groups. R and $R^1$ can also be part of a cyclic system.

The product monoester will exist as primary and secondary esters which rapidly equilibrate under the reaction conditions. Condensation of a mixture of aldehydes is also possible which will give rise to a mixture of 1,3-glycol monoesters.

Condensation of aldehydes to 1,3-glycol monoesters is a well known process that is currently practiced commercially. The catalyst for this reaction is generally an alkali metal alkoxide such as sodium isobutoxide as described in U.S. Pat. No. 3,091,632. The major disadvantage to this process is that carboxylic acid alkali metal salts and metal hydroxides are formed which may be difficult to remove from the reaction mixture. Also, aldehydes not possessing an alpha hydrogen give low yields of the desired 1,3-glycol monoester because of dehydration of the intermediate aldol product. The use of alkali metal or aluminum alkoxide catalysts requires the use of dry aldehydes because these catalysts react rapidly with water and are deactivated. Any dehydration that occurs during the reaction generates water which in turn deactivates the catalyst converting it to the alkali metal hydroxide and the corresponding alcohol. Removal of the alkoxide catalysts requires extraction and distillation steps that are costly to perform.

A two-step process is described in U.S. Pat. No. 3,367,966 in which the aldol is formed using a sodium hydroxide catalyst followed by a catalyst removal step. The aldol is then heated in the presence of an aldehyde in an autoclave to give a 1,3-glycol monoester. The yields of 1,3-glycol monoesters are low for aldehydes not possessing an alpha alkyl substituent. For example, n-butyraldehyde and n-butyraldol are converted to 2-ethylhexane-1,3-diol monobutyrate in 19.5 percent yield. The low yield results from extensive dehydration of the aldol intermediate.

Villani and Nord [JAC 68, 1674] describes the synthesis of 1,3-glycol monoesters in yields of 53.2 and 45.0 percent from acetaldehyde and isobutyraldehyde, respectively, using a magnesium-aluminum tetra-alkyl catalyst. The aldehydes used with this catalyst system must be anhydrous and the catalyst residues must be removed by extraction of decomposed with acid and removed by distillation.

Tin metal supported on silica gel is described as a vapor phase aldol catalyst by Swift, Bozik, and Massota, in Catalysis 15 407 (1969). Swift also describes the vapor phase reaction of n-butyraldehyde with tin metal supported on silica gel in U.S. Pat. No. 3,542,878. The product of the reaction is 2-ethylhexenal in 95 percent selectivity, at 40 percent n-butyraldehyde conversion. Japanese workers have described the simple Tischenko reaction of aldehydes in Japan Kokai No. 76/39,619 using dibutyltin oxide. The products claimed were simple esters, for example, n-butyraldehyde reacted in the presence of dibutyltin oxide to form butylbutyrate in approximately 45 percent yield. The catalyst and process described by this invention produce only traces of simple esters (less than 1 percent).

The use of tin metal or tin salts as catalysts for the aldol-Tischenko reaction of aldehydes from the preparation of 1,3-glycol monoesters has not been previously reported. The advantages of using this catalyst system over conventional catalysts include: higher yields of 1,3-glycol monoester for the reaction of aldehydes that form an easily dehydratable aldol; elimination of soluble metal salts and metal hydroxides as by-products of the reaction; and the capability of conducting the reaction in a single step. A catalyst removal step is unnecessary using the catalyst and process described in this invention.

In view of the above, it was therefore quite surprising to one trained in the art that aldehydes could be condensed to form 1,3-glycol monoesters utilizing a tin metal or tin oxide catalyst. The ease of dehydration of the intermediate aldol products indicates that the favored reaction should be formation of the enal by dehydration. The vapor phase condensation of aldehydes such as n-butyraldehyde described in U.S. Pat. No. 3,542,878 results in the formation of the dehydration product, 2-ethylhexenal, in 95 percent selectivity. This is in sharp contrast with the results obtained using the instant invention in which the condensation of n-butyraldehyde in the liquid phase utilizing the process of the instant invention produces 2-ethylhexane 1,3-diol monobutyrate in 88% selectivity.

The effect of the tin catalyst is also surprising in view of Japanese Kokai No. 76/39,619 which describes the formation of simple esters resulting from a Tischenko reaction utilizing tin salts such as dibutyltin oxide as a catalyst. This work describes formation of simple esters such as n-butylbutyrate from n-butyraldehyde. In the process of the instant invention less than 1% simple esters are formed.

Tin esters are also known to be excellent catalysts for ester interchange. Therefore, it is surprising that monoesters are the principal product of the instant invention and there is no evidence of extensive ester interchange occurring under reaction conditions to produce diols and diesters. A major advantage of the instant invention is the fact that it produces 1,3-glycol monoesters in high yield without the production of metal salts or metal hydroxides. The removal of catalyst residues or soluble salts is unnecessary with the instant invention. The yield of 1,3-glycol monoesters using the instant invention is 70-80%. The yield using aldehydes that do not have an alkyl group in the beta position is much higher than that obtained by any other known method.

According to the process of the instant invention three molecules of the same or different aldehydes designated as A, B and C having the formulas

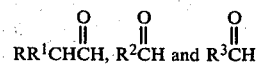

respectively wherein R, $R^1$, $R^2$ and $R^3$ are as defined below, are condensed in the liquid phase in the presence of a catalyst consisting of tin metal or tin oxide to produce a 1,3-glycol monoester. When the three molecules are all the same aldehyde the reaction will be as follows:

When the reaction is between a first aldehyde A, a second aldehyde B and an aldehyde C which is the same as either aldehyde A or aldehyde B a complex mixture of glycol 1,3-monoesters will be produced. This mixture can be depicted according to the following formula:

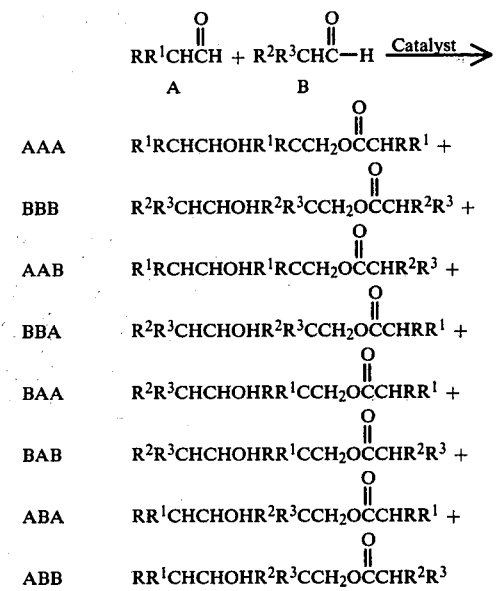

The complexity of the reaction products will be reduced when one of the aldehydes being condensed does not have an alpha hydrogen. Condensations of this type can be represented by the following expression:

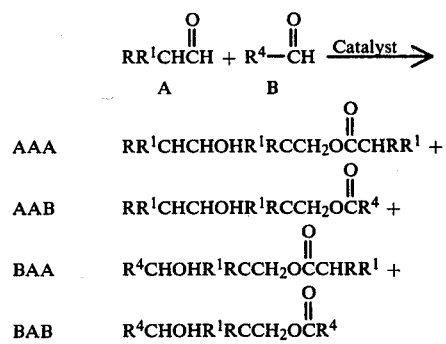

In each of the above R, $R^1$, $R^2$ and $R^3$ may be hydrogen, or a straight or branched alkyl or cycloalkyl moiety of from 1 to 20 carbon atoms or an aryl moiety of from 6 to 10 carbon atoms or the R substituents on any carbon atom ($R-R^1$, $R^2-R^3$) may be joined so as to include the carbon atom into a cyclic group of from 6–10 carbon atoms. $R^4$ may be the same as any of the substituents described for R, $R^1$, $R^2$ and $R^3$ except that $R^4$ cannot be any substituent which would result in the aldehyde having an alpha-hydrogen. Typical R substituents may be methyl, ethyl, propyl, normal or isobutyl, straight or branched chained pentyl, phenyl, benzyl, naphthyl, cyclopentyl and cyclohexyl.

In the event that aldehyde C is not the same as either aldehyde A or B an even more complex mixture of reaction products will be obtained consisting of all possible combinations of the three aldehydes A, B and C.

The catalyst for the condensation can be tin or tin oxide either unsupported or supported on a suitable support such as silica gel or alumina. The purpose of the support is to increase the surface area of the tin metal or tin oxide.

The reaction is carried out by contacting the aldehyde with the catalyst at a temperature of 65° C. to 200° C. and a pressure high enough to keep the aldehyde in the liquid phase. For low boiling aldehydes, such as acetaldehyde, pressures of 200 to 300 psig were found to be suitable. Higher boiling aldehydes, such as valeraldehyde, can be converted to 1,3-glycol monoesters at their reflux temperatures at atmospheric pressure. The preferred temperature for the reaction is 70° C. to 180° C., depending on the structure of the aldehyde. The catalyst can be employed as a slurry or suspension or as a fixed bed in which the aldehyde is passed over the catalyst bed. The reaction time is generally from 1 hour to 24 hours, depending on the temperature employed. The reaction can easily be carried out in a continuous fashion by feeding fresh aldehyde and catalyst to the reaction mixture and removing the product at the same rate. The resulting mixture of unreacted aldehyde and 1,3-glycol monoester can be separated conveniently by distillation. The aldehyde does not need to be anhydrous which is advantageous because it eliminates extensive drying steps that must be employed in reactions of this type which employ metal alkoxide catalysts. Anhydrous aldehydes can be employed for the reaction and usually react at lower temperatures (70° C.–100° C.) than when water is present.

The reaction allows the preparation of 1,3-glycol monoesters in high yields in a single step. Unreacted aldehyde can be recycled to the reactor. Side reactions such as dehydration to form alpha-beta-unsaturated aldehydes by dehydration of the intermediate aldol product are minimized using the catalyst and process of this invention. Significantly, concentrations of soluble tin salts are less than 200 ppm in the reaction products. The tin can be removed conveniently by distillation without decomposition of the 1,3-glycol monoester. Conventional Tischenko catalysts, such as aluminum or sodium alkoxides, must be separated from the reaction mixture by extraction or flash distillation to obtain maximum yields of 1,3-glycol monoesters. Traces of sodium salts lead to extensive decomposition of the 1,3-glycol monoesters upon distillation.

The 1,3-glycol monoesters prepared using the method of this invention are known compounds with established usefulness as coalescing aids for paints, as solvents and as plasticizers. They can also be used as precursors in the preparation of 1,3-glycols, diesters and polyesters.

The process of the instant invention is illustrated in greater detail by the following examples. It is understood that these examples are not intended to limit the invention in any way. Obvious modifications will occur to those skilled in the art.

EXAMPLE 1—Tin Metal Catalyzed Synthesis of 2-Ethylhexane-1,3-diol Butyrate

The purpose of this example is to demonstrate the use of tin metal as a catalyst for the conversion of n-butyraldehyde to 2-ethylhexane-1,3-diol monobutyrate. A 300 milliliter stainless steel autoclave is charged with 120 grams of n-butyraldehyde containing 2 weight percent water. Granular tin metal, 20 mesh (2.4 grams, 2.0 weight percent) is added. The autoclave is pressured to 100 psig nitrogen and heated to 160° C. with stirring for 2 hours. The autoclave is then cooled and vented. The liquid products recovered weigh 117 grams. The reactor contents contain 0.6 ppm soluble tin. Distillation of the reactor contents produces 66 grams of n-butyraldehyde (45 percent aldehyde conversion), 3 grams of water, 4.4 grams of 2-ethylhexenal (9 mole percent yield), 2 grams of n-butyraldol (boiling point 74° C.–78° C. per 1 mm), 39.6 grams of 2-ethylhexane-1,3-diol monobutyrate (88 mole percent yield) boiling point 105° C.–114° C. per 1 mm.

EXAMPLE 2—Stannous Oxide Catalyzed Synthesis of 2-Ethylhexane-1,3-diol Butyrate The purpose of this example is to demonstrate the use of stannous oxide as a catalyst for the conversion of n-butyraldehyde to 2-ethylhexane-1,3-diol monobutyrate. The conditions of Example 1 are followed except that 2.4 grams (2 weight percent) of stannous oxide powder (100 mesh) are used in place of tin metal as the catalyst. The n-butyraldehyde conversion is 40 percent. The yield of 2-ethylhexane-1,3-diol monobutyrate was 88 percent and the yield of 2-ethylhexenal is 10 mole percent. The crude rection mixture contains 1 ppm soluble tin.

EXAMPLE 3—Tin Metal Catalyzed Synthesis of 2-methylpentane-1,3-diol Monopropionate The purpose of this example is to demonstrate that propionaldehyde can be converted to 2-methylpentane-1,3-diol monopropionate with a tin catalyst. In a 1 gallon Magnedash autoclave is charged 1,500 grams of propionaldehyde and 30 grams of granular tin metal (20 mesh). The autoclave is pressured to 100 psig nitrogen and heated to 160° C. for 3 hours. The pressure rises to 285 psig. The reactor is cooled and vented. The products contain less than 1 ppm of soluble tin. The aldehyde is 32 percent converted to products. The yield of 2-methylpentane-1,3-diol monopropionate is 345 grams (72 mole percent) boiling point 76° C.–81° C. per 1 mm, and the yield of 2-methylpentenal is 21 grams (5 mole percent). Propionaldol is isolated in 11 percent yield (boiling point 47° C. per 1 mm).

EXAMPLE 4—Tin Metal Catalyzed Synthesis of Butane-1,3-diol Monoacetate

The purpose of this example is to demonstrate that acetaldehyde can be converted to butane-1,3-diol monoacetate with a tin catalyst. The procedure of Example 3 is used except that the temperature is maintained at 170° C. The acetaldehyde is 30 percent converted to products. The yield of butane-1,3-diol monoacetate is 70 percent (boiling point 47° C.–61° C. per 1 mm), and the yield of crotonaldehyde is 7 mole percent. Acetaldol is obtained in 12 percent yield.

EXAMPLE 5—Stannous Oxide Catalyzed Synthesis of 2,2,4-Trimethylpentane-1,3-diol Monoisobutyrate The purpose of this example is to demonstrate the use of stannous oxide as a catalyst for the conversion of isobutyraldehyde to 2,2,4-trimethylpentane-1,3-diol monoisobutyrate. The conditions of Example 2 are employed except that isobutyraldehyde containing 2 weight percent water is used instead of n-butyraldehyde and the temperature is maintained at 180° C. The aldehyde is 28 percent converted to products. The yield of 2,2,4-trimethylpentane-1,3-diol monoisobutyrate is 90 percent (boiling point 94° C. per 1 mm). Isobutanol is formed in 4 percent yield.

EXAMPLE 6—Tin Metal on Silica Gel Catalyzed Synthesis of 2-Ethylhexane-1,3-diol Monobutyrate From Dry Butyraldehyde The purpose of this example is to demonstrate that dry aldehydes react at moderate temperatures to form 1,3-glycol monoacetates. n-Butyraldehyde is dried by azeotropic distillation. The dry aldehyde, 50 milliliters, and 10 grams of 9 percent tin on silica gel, are heated under reflux for 16 hours. The temperature rises from 74° C. to 107° C. The aldehyde is 85 percent converted to products. The yield of 2-ethylhexane-1,3-diol monobutyrate is 83 percent. The diester is obtained in 6 percent yield and 2-ethylhexenal is obtained in 5 percent yield.

EXAMPLE 7—Tin Catalyzed Synthesis of 2-Ethylhexane-1,3-diol Monobutyrate in Continuous Process The purpose of this example is to demonstrate that the synthesis of 2-ethylhexane-1,3-diol monobutyrate can be carried out continuously. A 300 milliliter stainless steel autoclave is fitted with a stainless steel screen catalyst basket containing 20 grams of 20 mesh granular tin catalyst. n-Butyraldehyde is pumped continuously to the stirred liquid full, autoclave and the product mixture is removed through a pressure controlled research valve. The pressure is maintained at 180 psig and the temperature of the reactor contents is maintained at 155° C. The average residence time of n-butyraldehyde in the reactor is 6 hours. Under these conditions the n-butyraldehyde conversion is 58 percent. The yield of 2-ethylhexane-1,3-diol monobutyrate is 84 percent. The yield of 2-ethylhexenal is 5 percent and the yield of n-butyraldol is 6 percent.

EXAMPLE 8—Tin Catalyzed Synthesis of 2,2-Dimethylpropane-1,3-diol Monoisobutyrate The purpose of this example is to demonstrate the synthesis of a 1,3-glycol monoester from a mixture of aldehydes. A 300 milliliter autoclave is charged with 100 grams (1.39 moles) of isobutyraldehyde, 28.2 grams (0.35 mole) of 37 percent formalin solution and 2.4 grams of 20 mesh granular tin metal. The autoclave is pressured to 100 psig with nitrogen and heated to 160° C. for 2 hours. The reactor is cooled and vented. The recovered weight is 123 grams of liquid products. The formaldehyde is 100 percent converted to products and the isobutyraldehyde is 35 percent converted to products. The yield of 2,2-dimethylpropane-1,3-diol monoisobutyrate is 60 percent. 2,2-Dimethylpropane-1,3-diol is obtained in 8 percent yield and 5,5-dimethyl-3-isopropyl-1,3-dioxane is obtained in 15 yield weight percent yield.

EXAMPLE 9—Tin on Silica Gel Catalyzed Synthesis of 2-Ethylhexane-1,3-diol Monobutyrate The purpose of this experiment is to demonstrate the use of supported tin catalyst for the condensation of n-butyraldehyde. The catalyst is prepared by impregnating extruded silica gel (Houdry) with stannous chloride (1.61 grams stannous chloride per gram of silica gel) followed by calcination at 450° C. for 48 hours and reduction in hydrogen for 48 hours at 350° C. Catalyst prepared in this manner has a tin concentration of 9.2 weight percent.

The catalyst is evaluated as described in Example 1 (4 grams of catalyst per 120 grams of n-butyraldehyde). The conversion of n-butyraldehyde is 48 percent. The yield of 2-ethylhexane-1,3-diol monobutyrate is 82 percent and the yield of 2-ethylhexenal is 14 percent.

The instant invention has been described in detail with particular reference to certain preferred embodiments thereof, but it will be understood that variations and modifications can be effected in the spirit and scope of the invention as described hereinabove and as defined in the appended claims.

We claim:

1. A process for manufacturing 1,3-glycol monoesters wherein a molecule of each of the aldehydes A, B and C is reacted in the presence of a catalyst consisting of metallic tin or stannous oxide at a temperature of from about 70° C. to about 180° C. and a pressure at least sufficient to maintain the aldehydes in a liquid phase wherein A is an aldehyde of the formula $$RR^1CHCH,\overset{O}{\overset{\|}{}}$$

B is an aldehyde of the formula $$R^2\overset{O}{\overset{\|}{C}}H$$

and C is an aldehyde of the formula $$R^3\overset{O}{\overset{\|}{C}}H$$

wherein R, $R^1$, $R^2$ and $R^3$ may be hydrogen or a straight or branched alkyl or cycloalkyl moiety of from 1 to 20 carbon atoms or an aryl moiety of from 6 to 10 carbon atoms or R and $R^1$ may be joined so as to include the carbon atom to which they are attached into a cyclic group of from 6–10 carbon atoms.

2. A process according to claim 1 wherein aldehyde A is selected from the group consisting of acetaldehyde, propionaldehyde, n-butyraldehyde, isobutyraldehyde and valeraldehyde and aldehyde B is selected from the group consisting of formaldehyde, acetaldehyde, propionaldehyde, n-butyraldehyde, isobutyraldehyde and valeraldehyde and aldehyde C is the same as either aldehyde A or aldehyde B.

3. A process according to claim 1 wherein the catalyst is metallic tin or stannous oxide supported on silica gel.

4. A process according to claim 1 wherein the aldehydes A, B and C are the same aldehyde.

5. A process according to claim 4 wherein the aldehydes A, B and C are selected from the group consisting of acetaldehyde, propionaldehyde, n-butyraldehyde, isobutyraldehyde, and valeraldehyde.

6. The process according to claim 5 where the aldehyde is n-butyraldehyde, the catalyst is tin on silica gel and the product 1,3-glycol monoester is 2-ethylhexane-1,3-diol monobutyrate.

7. A process according to claim 4 wherein the catalyst is metallic tin or stannous oxide supported on silica gel.